US012221402B2

(12) United States Patent
Becker et al.

(10) Patent No.: US 12,221,402 B2
(45) Date of Patent: Feb. 11, 2025

(54) METHOD FOR THE PRODUCTION OF ETHYLENEAMINES

(71) Applicant: BASF SE, Ludwigshafen am Rhein (DE)

(72) Inventors: Barbara Becker, Ludwigshafen am Rhein (DE); Thomas Heidemann, Ludwigshafen am Rhein (DE); Regine Helga Bebensee, Ludwigshafen am Rhein (DE); Eva Koch, Ludwigshafen am Rhein (DE); Johann-Peter Melder, Ludwigshafen am Rhein (DE); Hermann Luyken, Ludwigshafen am Rhein (DE); Claudia Oezkozanoglu, Ludwigshafen am Rhein (DE); Jens Kehrer, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 734 days.

(21) Appl. No.: 17/436,293

(22) PCT Filed: Feb. 26, 2020

(86) PCT No.: PCT/EP2020/054959
§ 371 (c)(1),
(2) Date: Sep. 3, 2021

(87) PCT Pub. No.: WO2020/178085
PCT Pub. Date: Sep. 10, 2020

(65) Prior Publication Data
US 2022/0177410 A1    Jun. 9, 2022

(30) Foreign Application Priority Data
Mar. 6, 2019   (EP) ................... 19160986

(51) Int. Cl.
| C07C 209/16 | (2006.01) |
| B01J 21/04 | (2006.01) |
| B01J 23/89 | (2006.01) |
| B01J 37/00 | (2006.01) |
| B01J 37/02 | (2006.01) |
| B01J 37/03 | (2006.01) |
| B01J 37/04 | (2006.01) |
| B01J 37/08 | (2006.01) |
| B01J 37/16 | (2006.01) |

(52) U.S. Cl.
CPC ............ *C07C 209/16* (2013.01); *B01J 21/04* (2013.01); *B01J 23/8986* (2013.01); *B01J 37/0009* (2013.01); *B01J 37/024* (2013.01); *B01J 37/03* (2013.01); *B01J 37/04* (2013.01); *B01J 37/082* (2013.01); *B01J 37/16* (2013.01)

(58) Field of Classification Search
None
See application file for complete search history.

(56) References Cited

U.S. PATENT DOCUMENTS

| 3,137,730 A | 6/1964 | Fitz-William |
| 4,111,840 A | 9/1978 | Best |
| 4,206,149 A | 6/1980 | Slaugh |
| 4,855,505 A | 8/1989 | Koell |
| 5,952,529 A | 9/1999 | Chang et al. |
| 5,958,825 A * | 9/1999 | Wulff-Doring ....... C07C 209/16 |
| | | 502/328 |
| 2010/0087682 A1 | 4/2010 | King et al. |

FOREIGN PATENT DOCUMENTS

| CN | 102190588 A | 9/2011 |
| CN | 102233272 A | 11/2011 |
| DE | 1172268 B | 6/1964 |
| EP | 0198699 B1 | 9/1989 |
| EP | 0526851 A2 | 2/1993 |
| EP | 0737514 A1 | 10/1996 |
| EP | 0839575 A2 | 5/1998 |
| EP | 1106600 A2 | 6/2001 |
| WO | 96/38226 A1 | 12/1996 |
| WO | 2000/006749 A2 | 2/2000 |
| WO | 2007/093514 A1 | 8/2007 |
| WO | 2008/006749 A1 | 1/2008 |
| WO | 2008/006750 A1 | 1/2008 |
| WO | 2009/008051 A1 | 1/2009 |
| WO | 2009/080506 A1 | 7/2009 |
| WO | 2009/080508 A1 | 7/2009 |
| WO | 2009/080510 A1 | 7/2009 |
| WO | 2011/067200 A1 | 6/2011 |
| WO | 2013/072289 A1 | 5/2013 |
| WO | 2018/224316 A1 | 12/2018 |
| WO | 2018/224321 A1 | 12/2018 |

OTHER PUBLICATIONS

Carsten Ihmels, "Studies on the Reaction Kinetics of the Metal Catalysed Amination of Ethylene Glycol in Liquid Phase", Diploma Thesis, Institut für Technische Chemie II, Universität Oldenburg (Germany) Catalysis Unit, Department of Chemical Engineering, University of Cape Town, Mar. 17, 2000, pp. 1-82.

(Continued)

*Primary Examiner* — Sudhakar Katakam
*Assistant Examiner* — Jennifer C Sawyer
(74) *Attorney, Agent, or Firm* — Faegre Drinker Biddle & Reath LLP

(57) ABSTRACT

The present invention relates to a process for preparing alkanolamines and ethyleneamines in the liquid phase, by reacting ethylene glycol and/or monoethanolamine with ammonia in the presence of an amination catalyst which is obtained by reducing a catalyst precursor, wherein the preparation of the catalyst precursor comprises a step a) in which a catalyst precursor comprising one or more catalytically active components of Sn, Cu and Ni, and a step b) in which the catalyst precursor prepared in step a) is contacted with a soluble Re compound.

14 Claims, No Drawings

(56) References Cited

OTHER PUBLICATIONS

International Search Report and Written Opinion received for PCT Patent Application No. PCT/EP2020/054959, mailed on May 6, 2020, 8 pages.

* cited by examiner

METHOD FOR THE PRODUCTION OF ETHYLENEAMINES

CROSS-REFERENCE TO RELATED APPLICATIONS

This application is a national stage application (under 35 U.S.C. § 371) of PCT/EP2020/054959, filed Feb. 26, 2020, which claims benefit of European Application No. 19160986.6, filed Mar. 6, 2019, both of which are incorporated herein by reference in their entirety.

The present invention relates to a process for preparing alkanolamines and ethyleneamines, especially ethylenediamine.

Two processes are generally employed for industrial scale preparation of ethylenediamine (EDA).

Firstly, EDA can be prepared by reaction of 1,2-dichloroethane with ammonia with elimination of HCl (EDC process). A further industrial scale process for preparation of EDA is the reaction of monoethanolamine (MEA) with ammonia in the presence of amination catalysts (MEA process).

As an alternative to the established processes, EDA can also be prepared by reaction of monoethylene glycol (MEG) with ammonia.

Such a process would have various advantages. One advantage is the good availability of MEG compared to MEA.

MEA is prepared on the industrial scale by reaction of ethylene oxide (EO) and ammonia. What is generally formed is a reaction mixture comprising, as well as MEA, also higher ethanolamines such as diethanolamine (DEOA) and triethanolamine (TEOA). These by-products have to be separated from MEA by a separate distillation step. Ethylene oxide is a highly flammable gas that can form explosive mixtures with air. The handling of EO is correspondingly complex. The preparation of MEA thus requires a technically complex EO plant with downstream purifying distillation.

By contrast, MEG can be produced either on the basis of petrochemical raw materials or on the basis of renewable raw materials. By petrochemical means, MEG is likewise prepared from EO by reaction with water. In the same way as in the reaction of EO with ammonia, it is not possible in the reaction of EO with water to prevent MEG that has already formed from reacting with EO to give by-products such as di- and triethylene glycol. The selectivity for MEG is about 90% and is thus, however, distinctly higher than the selectivity for MEA, which is generally 70-80%. The Shell omega process once again distinctly increased the selectivity for MEG—to about 99%. In the omega process, EO is reacted with $CO_2$ to give ethylene carbonate which, in the second step, is selectively hydrolyzed to MEG.

MEG can also be prepared via the synthesis gas route, for example by oxidative carbonylation of methanol to give dimethyl oxalate and subsequent hydrogenation thereof. Thus, a further possible petrochemical raw material for the preparation of MEG is also natural gas or coal.

Alternatively, MEG can also be prepared from renewable raw materials, such as corn or sugarcane, by fermentation to ethanol, followed by dehydration to ethene and subsequent reaction with oxygen to give ethylene oxide.

Owing to the many production variants, the availability of MEG is generally high, which generally has a positive effect on raw material costs.

The prior art discloses that the reaction of MEG with ammonia to give EDA can be effected either in the liquid phase or in the gas phase.

The amination of MEG in the gas phase is disclosed in the two Chinese applications CN 102 190 588 and CN 102 233 272.

For instance, CN 102 190 588 describes the one-stage conversion of MEG and ammonia in the presence of Cu catalysts. According to the description, the reaction pressure is within a range from 3 to 30 bar. The reaction temperature is in the range from 150 to 350° C.

Application CN 102 233 272 discloses the reaction of MEG with ammonia in the gas phase over catalysts that include Cu and Ni as main constituents and Zr, Zn, Al, Ti, Mn and Ce as secondary component. However, the composition of the reaction mixtures obtained was not disclosed.

As an alternative to conversion in the gas phase, the reaction of MEG with ammonia and hydrogen can also be effected in the liquid phase. However, there is generally a considerable difference in the reaction characteristics of catalysts in the gas phase and liquid phase, and so it is generally impermissible to apply conclusions from the reaction characteristics of MEG in the gas phase to the reaction characteristics of MEG in the liquid phase.

An overview of the metal-catalyzed amination of MEG in the liquid phase is given in the Diplom thesis "Reaktionskinetische Untersuchungen zur metallkatalysierten Aminierung von Ethylenglykol in der flüssigen Phase" [Studies of Reaction Kinetics of the Metal-Catalyzed Amination of Ethylene Glycol in the Liquid Phase] by Carsten Wolfgang Ihmels ("Reaktionskinetische Untersuchungen zur metallkatalysierten Aminierung von Ethylenglykol in der flüssigen Phase", Diplom thesis from the Carl von Ossietzky University of Oldenburg dated Mar. 17, 2000). Ihmels describes a multitude of further reactions and side reactions that can occur in the amination of MEG, for example the formation of di- and triethanolamine, disproportionation, nitrile formation, carbonyl condensation and fragmentation reactions. Condensation and disproportionation in the case of dihydric alcohols can ultimately also lead to the formation of oligomers, such as diethylenetriamine (DETA), triethylenetetramine (TETA) and polymers. An important further side reaction is cyclization. For instance, diethanolamine or DETA can react further to give piperazine (PIP). Higher temperatures promote dehydrogenation, which follows on from the cyclization, to give aromatics. Thus, the reaction of MEG with ammonia gives a broad product spectrum, some products in the product spectrum being of greater commercial interest than others. For instance, the commercial demand for EDA, DETA and TETA is higher than that for PIP or aminoethylethanolamine (AEEA). The object of many studies in the reaction of MEG with ammonia was therefore to find catalysts and reaction conditions that lead to an advantageous product spectrum.

Ihmels himself studied the conversion of MEG over supported cobalt/silicon dioxide catalysts. Amination to give the desired MEA and EDA target product was unsuccessful. Instead, high-polymeric reaction products were formed. Under milder conditions, still with incomplete conversion of MEG, the target products MEA and EDA were obtained in low yields.

The main products were oligomeric compounds.

U.S. Pat. No. 4,111,840 discloses the reaction of MEG with ammonia and hydrogen at pressures of 500 to 5000 psig (about 34 to 340 bar) over supported Ni/Re catalysts. Supported silica/alumina catalysts having a surface area of 60 m²/g led to better results here than supported silica/alumina catalysts having a specific surface area of 150 m²/g.

U.S. Pat. No. 3,137,730 discloses the reaction of MEG with ammonia in the liquid phase at temperatures of 200-300° C. and pressures above 1000 psig (about 69 bar) over Cu/Ni catalysts.

DE 1 172 268 discloses the conversion of ethylene glycol over catalysts comprising at least one of the metals Cu, Ag, Mn, Fe, Ni and Co. In one example, MEG was reacted with ammonia at 180° C. and a pressure of 300 bar in the presence of hydrogen over a Co catalyst.

WO 2007/093514 discloses a two-stage process for preparing EDA, wherein, in the first process stage, the amination is conducted over a hydroamination catalyst up to an MEA conversion of not more than 40% and, in the second process stage, a supported shaped Ru/Co catalyst body having small geometry is used and the second stage is conducted at a temperature at least 10° C. higher than the first process stage.

Catalysts for the amination of alcohols that comprise Sn are likewise disclosed in WO 2011067200. The catalysts described therein comprise not only Sn but also the elements Co, Ni, Al and Cu.

Further catalysts for the amination of alcohols are disclosed in WO 200908051, WO 2009080508, WO 200006749 and WO 20008006750. The catalysts comprise not only Zr and Ni but also Cu, Sn, Co and/or Fe. Further constituents are elements such as V, Nb, S, O, La, B, W, Pb, Sb, Bi and In.

WO 2013072289 discloses the reaction of alcohols with a nitrogen compound over catalysts that include the element Sn in addition to Al, Cu, Ni and Co. Preferred alcohols mentioned are ethylene glycol and monoethanolamine. The catalysts are obtained by precipitative application of solutions of the respective metal salts on a catalyst support.

U.S. Pat. No. 4,855,505 discloses the amination of MEG and MEA in the presence of catalysts comprising Ni and/or Co and Ru. This involves contacting a catalyst precursor comprising Ni oxide and/or Co oxide with an Ru halide, for example Ru chloride, and then reducing it in a hydrogen stream.

EP 0 839 575 discloses catalysts comprising Co, Ni and mixtures thereof and Ru on a porous metal oxide support. The catalysts are prepared by impregnating the support with the metals, drying and calcining the impregnated support and reducing the calcined support in a hydrogen stream. It is further disclosed that the support can be impregnated with metal compounds in any sequence. In one example, a support is first impregnated with a solution of Ni nitrates, Co nitrates and Cu nitrates, then calcined and further impregnated with an aqueous Ru nitrate solution.

WO 96/38226 discloses catalysts for the amination of alcohols that comprise Re, Ni, Co, B, Cu and/or Ru. In one example, a support of $SiO_2$ is impregnated with a solution of $NH_4ReO_4$, Ni nitrate, $H_3BO_3$, Co nitrate and Cu nitrate and then calcined. In a further impregnation step, the calcined and impregnated support is impregnated with Ru chloride.

Catalysts for the amination of ethylene glycol are disclosed in WO 2018/224321 which are obtained by impregnation of a catalyst precursor, comprising at least one metal selected from Sn, Cu or Ni, with a soluble Ru-compound and with a soluble Co-compound.

It was an object of the present invention to develop a heterogeneous catalyst for the amination of MEG and/or MEA in the liquid phase that shows adequate activity and selectivity in the conversion of MEG to MEA and/or EDA.

More particularly, the formation of products of value, i.e. those ethanolamines or ethyleneamines with a high commercial significance, especially MEA and EDA, was to be promoted and the formation of cyclic ethyleneamines, especially PIP, and higher ethanolamines, especially AEEA, was to be kept low since the commercial demand for PIP or AEEA is lower than for EDA and MEA.

More particularly, the concentration of particular unwanted by-products, such as NMEDA, NEEDA and ethylamine (EA), was also to be reduced. NMEDA has a volatility that barely differs from EDA, and so the two components are separable only with high separation complexity. It would thus be advantageous if only small amounts of NMEDA were to be formed even in the production. The customary product specifications of EDA require that less than 500 ppm of NMEDA be present in EDA.

In addition, the catalysts were also to have high activity and enable high MEG conversion in order to achieve a good space-time yield.

Overall, a good spectrum of properties in relation to overall selectivity, selectivity quotient and the formation of unwanted by-products was thus to be achieved.

The object of the present invention was achieved by a process for preparing alkanolamines and ethyleneamines in the liquid phase, by reacting ethylene glycol and/or monoethanolamine with ammonia in the presence of an amination catalyst which is obtained by reducing a catalyst precursor, wherein the preparation of the catalyst precursor comprises a step a) in which a catalyst precursor comprising one or more catalytically active components of Sn, Cu and Ni is prepared, and a step b) in which the catalyst precursor prepared in step a) is contacted with a soluble Re compound.

It has been surprisingly found that amination catalysts that are prepared in accordance with the invention by contacting a catalyst precursor comprising Ni, Sn or Cu with a soluble Re-compound have high selectivity for the linear amination products MEA and EDA, while the selectivity for the cyclic amination product PIP and the higher ethanolamine AEEA is low, compared to amination catalysts that are prepared by contacting a catalyst precursor comprising Ni, Sn and/or Cu with a Ru-compound and a Co-compound.

In addition, it has been found that catalysts of the invention form a lower level of unwanted by-products, such as NMEDA. Moreover, it has been found that the amination catalysts used in the process of the invention have a high activity for the conversion of MEG and hence enable high space-time yields in the conversion.

The following abbreviations are used above and hereinafter:

AEEA: aminoethylethanolamine
AEP: aminoethylpiperazine
DETA: diethylenetriamine
EA: ethylamine
EDA: ethylenediamine
EO: ethylene oxide
HEP: hydroxyethylpiperazine
NEEDA: N-ethylethylenediamine
NMEDA: N-methylethylenediamine
MEA: monoethanolamine
MEG: monoethylene glycol
PIP: piperazine
TEPA: tetraethylenepentamine
TETA: triethylenetetramine Amination Catalysts:

The process of the invention for preparing alkanolamines and ethyleneamines by reaction of MEG and/or MEA with $NH_3$ is effected in the presence of amination catalysts.

Catalyst Precursors:

The amination catalysts are obtained by reduction of catalyst precursors.

The preparation of the catalyst precursor comprises 2 steps.

In a step a), a catalyst precursor comprising one or more catalytically active components of Sn, Cu and Ni is first prepared.

The catalyst precursor obtained in step a) is contacted with a soluble Re compound in a further step b).

Step a) Preparation of the Catalyst Precursor:

Active Composition:

The catalyst precursors comprise an active composition.

The active composition of the catalyst precursors comprises one or more active metals and optionally one or more added catalyst elements, and also optionally one or more support materials.

Active Metals:

According to the invention, the active composition of the catalyst precursors used in the process of the invention comprises one or more active metals selected from the group consisting of Sn, Cu and Ni.

Added Catalyst Elements:

The active composition of the catalyst precursors used in the process of the invention may optionally comprise one or more added catalyst elements.

The added catalyst elements are metals or semimetals selected from groups 1 to 8, 9, 10 (excluding Ni), 11 (excluding Cu) and 12 to 13, 14 (excluding Sn) and 15 to 17 of the Periodic Table, the element P and the rare earth metals.

Preferred added catalyst elements are Co, Zr, Al, Fe, Sb, Pb, Bi, In, Ga, V, Nb, S, P, B, W, La, Ce, Y and Hf.

Particularly preferred added catalyst elements are Co, Zr, Al and Fe.

In a very particularly preferred embodiment, the added catalyst element is Co.

Catalytically Active Components:

In the catalyst precursor, the active metals and the added catalyst elements are generally in the form of their oxygen compounds, for example of carbonates, oxides, mixed oxides or hydroxides of the active metals or added catalyst elements.

The oxygen compounds of the active metals and of the added catalyst elements are referred to hereinafter as catalytically active components.

However, the term "catalytically active components" is not intended to imply that these compounds are already catalytically active per se. The catalytically active components generally have catalytic activity in the inventive conversion only after reduction of the catalyst precursor.

In general, the catalytically active components are obtained by a conversion of the soluble compounds of the active metals or of the added catalyst elements or precipitates of the active metals or of the added catalyst elements through calcination, the conversion generally being effected by dewatering and/or decomposition.

Support Materials:

The catalytically active composition may further comprise one or more support materials.

The support materials are generally added catalyst elements which are used in solid form in the preparation of the catalyst precursors and onto which the soluble compounds of the active metals and/or added catalyst elements are precipitated or which are impregnated with the soluble compounds of the active metals or added catalyst elements. In general, support materials are solids having a high surface area.

Preference is given to using support materials that already have the preferred shape and geometry described hereinafter (see section "Shape and geometry of the support materials and catalyst precursors").

The catalytically active components can be applied to the support material, for example by precipitative application of the active metals or of the added catalyst elements in the form of their sparingly soluble compounds, for example the carbonates, hydrogencarbonates or hydroxides, or by impregnating the support material with soluble compounds of the active metals or added catalyst elements.

The support material used may be the added catalyst element carbon, for example in the form of graphite, carbon black and/or activated carbon.

Preferred support materials are oxides of the added catalyst elements Al, Ti, Zn, Zr and Si or mixtures thereof, for example aluminum oxide (gamma, delta, theta, alpha, kappa, chi or mixtures thereof), titanium dioxide (anatase, rutile, brookite or mixtures thereof), zinc oxide, zirconium dioxide, silicon dioxide (such as silica, fumed silica, silica gel or silicates), aluminosilicates, minerals, such as hydrotalcite, chrysotile and sepiolite.

Particularly preferred support materials are aluminum oxide or zirconium oxide or mixtures thereof.

A particularly preferred support material is aluminum oxide.

Composition of the Catalyst Precursors:

The catalyst precursors used in the process are used preferably in the form of catalyst precursors which consist only of catalytically active composition and optionally a shaping aid (such as graphite or stearic acid, for example) if the catalyst precursor is used in the form of shaped bodies.

The proportion of the catalytically active composition based on the total mass of the catalyst precursor is typically 70% to 100% by weight, preferably 80% to 100% by weight, more preferably 90% to 100% by weight, even more preferably 95% by weight to 100% by weight and more preferably 97% by weight to 100% by weight.

The composition of the catalyst precursors can be measured by means of known methods of elemental analysis, for example of atomic absorption spectrometry (AAS), of atomic emission spectrometry (AES), of X-ray fluorescence analysis (XFA) or of ICP-OES (Inductively Coupled Plasma Optical Emission Spectrometry).

The concentration figures (in % by weight) of the catalytically active components in the context of the present invention are reported as the corresponding oxide.

The added catalyst elements of group 1 (alkali metals) are calculated as $M_2O$, for example $Na_2O$.

The added catalyst elements of group 2 (alkaline earth metals) are calculated as MO, for example MgO or CaO.

The added catalyst elements of group 13 (boron group) are calculated $M_2O_3$, for example $B_2O_3$ or $Al_2O_3$.

In the carbon group (group 14), Si is calculated as $SiO_2$, Ge as GeO, Sn as SnO and Pb as PbO.

In the nitrogen group (group 15), P is calculated as $H_3PO_4$, As as $As_2O_3$, Sb as $Sb_2O_3$ and Bi as $Bi_2O_3$.

In the group of the chalcogens (group 16), Se is calculated as $SeO_2$ and Te as $TeO_2$.

In the scandium group (group 3), Sc is calculated as $Sc_2O_3$, Y as $Y_2O_3$ and La as $La_2O_3$.

In the titanium group (group 4), Ti is calculated as $TiO_2$, Zr as $ZrO_2$ and Hf as $HfO_2$.

In the vanadium group (group 5), V is calculated as $V_2O_5$, Nb as $Nb_2O_5$ and Ta as $Ta_2O_5$.

In the chromium group (group 6), Cr is calculated as $CrO_2$, Mo as $MoO_3$ and W as $WO_2$.

In the manganese group (group 7), Mn is calculated as $MnO_2$ and Re as $ReO_3$.

In the iron group (group 8), Fe is calculated as $Fe_2O_3$, Ru as $RuO_2$ and Os as $OsO_4$.

In the cobalt group (group 9), Co is calculated as CoO, Rh as $RhO_2$ and Ir as $IrO_2$.

In the nickel group (group 10), Ni is calculated as NiO, Pd as PdO and Pt as PtO.

In the copper group (group 11), Cu is calculated as CuO, Ag as AgO and Au as $Au_2O_3$.

In the zinc group (group 12), Zn is calculated as ZnO, Cd as CdO and Hg as HgO.

The concentration figures (in % by weight) of the components of the catalyst precursor are each based—unless stated otherwise—on the catalytically active composition of the catalyst precursor after the last calcination thereof and prior to contacting of the calcined catalyst precursor with the soluble Re compound.

The composition of the catalyst precursors is generally dependent on the preparation method described hereinafter (coprecipitation or precipitative application or impregnation).

Catalyst precursors that are prepared by coprecipitation do not comprise any support material. If the precipitation, as described hereinafter, is effected in the presence of a support material, the precipitation is referred to in the context of the present invention as precipitative application.

Catalyst precursors that are prepared by coprecipitation comprise generally 1 to 3, more preferably 1 to 2 and especially preferably 1 active metal(s).

Irrespective of the number of active metals present in the active composition, in the case of catalyst precursors that are prepared by coprecipitation, the composition of the catalytically active components of the active metals is preferably in the range from 1% to 95% by weight, more preferably 10% to 90% by weight, even more preferably 20% to 85% by weight and especially preferably 50% to 80% by weight, based on the total mass of the catalyst precursor, and where the catalytically active components are calculated as the oxide.

Catalyst precursors that are prepared by coprecipitation comprise generally 1 to 5, more preferably 1 to 4 and especially preferably 1 to 3 different added catalyst elements.

Irrespective of the number of added catalyst elements present in the active composition, in the case of catalyst precursors that are prepared by coprecipitation, the composition of the catalytically active components of the added catalyst elements is preferably in the range from 1% to 90% by weight, more preferably 5% to 80% by weight and most preferably 10% to 60% by weight, based on the total mass of the catalyst precursor, and where the catalytically active components are calculated as the oxide.

Catalyst precursors that are prepared by precipitative application comprise generally 5% to 95% by weight, preferably 10% to 80% by weight and more preferably 15% to 60% by weight of support material.

Catalyst precursors that are prepared by precipitative application comprise generally 1 to 3, more preferably 1 to 2 and especially preferably 1 active metal(s).

Irrespective of the number of active metals present in the active composition, in the case of catalyst precursors that are prepared by precipitative application, the composition of the catalytically active components of the active metals is preferably in the range from 5% to 90% by weight, more preferably 10% to 70% by weight and most preferably 15% to 60% by weight, based on the total mass of the catalyst precursor, and where the catalytically active components are calculated as the oxide.

Catalyst precursors that are prepared by precipitative application comprise generally 1 to 5, more preferably 1 to 4 and especially preferably 1 to 3 different added catalyst elements.

Irrespective of the number of added catalyst elements present in the active composition, in the case of catalyst precursors that are prepared by precipitative application, the composition of the catalytically active components of the added catalyst elements is preferably in the range from 1% to 80% by weight, more preferably 5% to 70% by weight and most preferably 10% to 50% by weight, based on the total mass of the catalyst precursor, and where the catalytically active components are calculated as the oxide.

Catalyst precursors that are prepared by impregnation comprise generally 50% to 99% by weight, preferably 75% to 98% by weight and more preferably 90% to 97% by weight of support material.

Catalyst precursors that are prepared by impregnation comprise generally 1 to 3, more preferably 1 to 2 and especially preferably 1 active metal(s).

Irrespective of the number of active metals present in the active composition, in the case of catalyst precursors that are prepared by impregnation, the composition of the catalytically active components of the active metals is preferably in the range from 1% to 50% by weight, more preferably 2% to 25% by weight and most preferably 3% to 10% by weight, based on the total mass of the catalyst precursor, and where the catalytically active components are calculated as the oxide.

Catalyst precursors that are prepared by impregnation comprise generally 1 to 5, more preferably 1 to 4 and especially preferably 1 to 3 different added catalyst elements.

Irrespective of the number of added catalyst elements present in the active composition, in the case of catalyst precursors that are prepared by impregnation, the composition of the catalytically active components of the added catalyst elements is preferably in the range from 1% to 50% by weight, more preferably 2% to 25% by weight and most preferably 3% to 10% by weight, based on the total mass of the catalyst precursor, and where the catalytically active components are calculated as the oxide.

Preferred catalyst precursor compositions:

Composition 1:

In a preferred embodiment, catalyst precursors wherein the catalytically active composition comprises catalytically active components of Zr, Cu and Ni and one or more catalytically active components of Sn, Pb, Bi and In are prepared. Catalyst precursors of this kind are disclosed, for example, in WO 2008/006749.

In a particularly preferred variant of this embodiment, a catalyst precursor comprising 10% to 75% by weight, preferably 25% to 65% by weight, more preferably 30% to 55% by weight, of catalytically active components of zirconium, calculated as $ZrO_2$, 1% to 30% by weight, preferably 2% to 25% by weight, more preferably 5% to 15% by weight, of catalytically active components of copper, calculated as CuO, 10% to 70% by weight, preferably 20% to 60% by weight, more preferably 30% to 50% by weight, of catalytically active components of nickel, calculated as NiO, 0.1% to 10% by weight, particularly in the range from 0.2% to 7% by weight, more particularly in the range from 0.4% to 5% by weight, very particularly in the range from 2% to 4.5% by weight, of catalytically active components of one or more metals selected from Sb, Pb, Bi and In, each calculated as $Sb_2O_3$, PbO, $Bi_2O_3$ and $In_2O_3$ respectively, is prepared.

Composition 2:

In a preferred embodiment, catalyst precursors wherein the catalytically active composition comprises catalytically active components Zr, Cu, Ni and Co and one or more catalytically active components of Pb, Bi, Sn, Sb and In are prepared. Catalyst precursors of this kind are disclosed, for example, in WO 2008/006750.

In a particularly preferred variant of this embodiment, a catalyst precursor comprising
10% to 75% by weight, preferably 25% to 65% by weight, more preferably 30% to 55% by weight, of catalytically active components of zirconium, calculated as $ZrO_2$,
1% to 30% by weight, preferably 2% to 25% by weight, more preferably 5% to 15% by weight, of catalytically active components of copper, calculated as CuO, and
10% to 70% by weight, preferably 13% to 40% by weight, more preferably 16% to 35% by weight, of catalytically active components of nickel, calculated as NiO,
10% to 50% by weight, preferably 13% to 40% by weight, more preferably 16% to 35% by weight, of catalytically active components of cobalt, calculated as CoO, and
0.1% to 10% by weight, particularly in the range from 0.2% to 7% by weight, more particularly in the range from 0.4% to 5% by weight, of catalytically active components of one or more metals selected from Pb, Bi, Sn, Sb and In, each calculated as PbO, $Bi_2O_3$, SnO, $Sb_2O_3$ and $In_2O_3$ respectively,
is prepared.

Composition 3:

In a further preferred embodiment, catalyst precursors wherein the catalytically active composition comprises catalytically active components of Zr, Ni and Fe and in the range from 0.2% to 5.5% by weight of one or catalytically active components of Sn, Pb, Bi, Mo, Sb and/or P, each calculated as SnO, PbO, $Bi_2O_3$, $MoO_3$, $Sb_2O_3$ and $H_3PO_4$ respectively, are prepared. Catalyst precursors of this kind are disclosed, for example, in WO 2009/080506.

In a particularly preferred variant of this embodiment, a catalyst precursor comprising
20% to 70% by weight of catalytically active components of zirconium, calculated as $ZrO_2$, 15% to 60% by weight of catalytically active components of nickel, calculated as NiO, and
0.5% to 14% by weight, preferably 1.0% to 10% by weight, more preferably 1.5% to 6% by weight, of catalytically active components of iron, calculated as $Fe_2O_3$, and
0.2% to 5.5% by weight, preferably 0.5% to 4.5% by weight, more preferably 0.7% to 3.5% by weight, of catalytically active components of tin, lead, bismuth, molybdenum, antimony and/or phosphorus, each calculated as SnO, PbO, $Bi_2O_3$, $MoO_3$, $Sb_2O_3$ and $H_3PO_4$ respectively,
is prepared.

Composition 4:

In a further preferred embodiment, catalyst precursors wherein the catalytically active composition comprises catalytically active components of Zr, Cu, Ni and
in the range from 0.2% to 40% by weight of catalytically active components of cobalt, calculated as CoO,
in the range from 0.1% to 5% by weight of catalytically active components of iron, calculated as $Fe_2O_3$, and
in the range from 0.1% to 5% by weight of catalytically active components of lead, tin, bismuth and/or antimony, each calculated as PbO, SnO, $Bi_2O_3$ and $Sb_2O_3$ respectively,
is prepared.

Catalyst precursors of this kind are disclosed, for example, in WO2009/080508.

In a particularly preferred variant of this embodiment, a catalyst precursor comprising
20% to 85% by weight, particularly 25% to 70% by weight, more particularly 30% to 60% by weight, of catalytically active components of zirconium, calculated as $ZrO_2$,
0.2% to 25% by weight, particularly 3% to 20% by weight, more particularly 5% to 15% by weight, of catalytically active components of copper, calculated as CuO,
0.2% to 45% by weight, particularly 10% to 40% by weight, more particularly 25% to 35% by weight, of catalytically active components of nickel, calculated as NiO,
0.2% to 40% by weight, preferably 1% to 25% by weight, more preferably 2% to 10% by weight, of catalytically active components of cobalt, calculated as CoO,
0.1% to 5% by weight, preferably 0.2% to 4% by weight, more preferably 0.5% to 3% by weight, of catalytically active components of iron, calculated as $Fe_2O_3$, and
0.1% to 5.0% by weight, particularly 0.3% to 4.5% by weight, more particularly 0.5% to 4% by weight, of catalytically active components of lead, tin, bismuth and/or antimony, each calculated as PbO, SnO, $Bi_2O_3$ and $Sb_2O_3$ respectively,
is prepared.

Composition 5:

In a further preferred embodiment, catalyst precursors wherein the catalytically active composition comprises catalytically active components Zr, Cu and Ni, and
in the range from 1.0% to 5.0% by weight of catalytically active components of cobalt, calculated as CoO, and
in the range from 0.2% to 5.0% by weight of catalytically active components of vanadium, niobium, sulfur, phosphorus, gallium, boron, tungsten, lead and/or antimony, each calculated as $V_2O_5$, $Nb_2O_5$, $H_2SO_4$, $H_3PO_4$, $Ga_2O_3$, $B_2O_3$, $WO_3$, PbO and $Sb_2O_3$ respectively,
is prepared.

Catalyst precursors of this kind are disclosed, for example, in WO2009/080508.

In a particularly preferred variant of this embodiment, a catalyst precursor comprising
46% to 65% by weight, particularly 47% to 60% by weight, more particularly 48% to 58% by weight, of catalytically active components of zirconium, calculated as $ZrO_2$,
5.5% to 18% by weight, particularly 6% to 16% by weight, more particularly 7% to 14% by weight, of catalytically active components of copper, calculated as CuO,
20% to 45% by weight, particularly 25% to 40% by weight, more particularly 30% to 39% by weight, of catalytically active components of nickel, calculated as NiO,
1.0% to 5.0% by weight, particularly in the range from 1.5% to 4.5% by weight, more particularly in the range from 2.0% to 4.0% by weight, of catalytically active components of cobalt, calculated as CoO, and
0.2% to 5.0% by weight, particularly 0.3% to 4.0% by weight, more particularly 0.5% to 3.0% by weight of catalytically active components of vanadium, niobium, sulfur, phosphorus, gallium, boron, tungsten, lead and/or antimony, each calculated as $V_2O_5$, $Nb_2O_5$, $H_2SO_4$, $H_3PO_4$, $Ga_2O_3$, $B_2O_3$, $WO_3$, PbO and $Sb_2O_3$ respectively, is prepared.

Composition 6:

In a further preferred embodiment, catalyst precursors wherein the catalytically active composition comprises catalytically active components of Al, Cu, Ni, Co and Sn and in the range from 0.2% to 5.0% by weight of catalytically active components of yttrium, lanthanum, cerium and/or hafnium, each calculated as $Y_2O_3$, $La_2O_3$, $Ce_2O_3$ and $Hf_2O_3$ respectively, are prepared.

Catalyst precursors of this kind are disclosed, for example, in WO 2011/067200.

In a particularly preferred variant of this embodiment, a catalyst precursor comprising 0.2% to 5.0% by weight, particularly in the range from 0.4% to 4.0% by weight, more particularly in the range from 0.6% to 3.0% by weight, even more particularly in the range from 0.7% to 2.5% by weight, of catalytically active components of tin, calculated as SnO, 10% to 30% by weight, more particularly in the range from 12% to 28% by weight, very particularly 15% to 25% by weight, of catalytically active components of cobalt, calculated as CoO, 15% to 80% by weight, particularly 30% to 70% by weight, more particularly 35% to 65% by weight, of catalytically active components of aluminum, calculated as $Al_2O_3$, 1% to 20% by weight, particularly 2% to 18% by weight, more particularly 5% to 15% by weight, of catalytically active components of copper, calculated as CuO, and 5% to 35% by weight, particularly 10% to 30% by weight, more particularly 12% to 28% by weight, very particularly 15% to 25% by weight, of catalytically active components of nickel, calculated as NiO, 0.2% to 5.0% by weight, particularly in the range from 0.4% to 4.0% by weight, more particularly in the range from 0.6% to 3.0% by weight, even more particularly in the range from 0.7% to 2.5% by weight, of catalytically reactive components of yttrium, lanthanum, cerium and/or hafnium, each calculated as $Y_2O_3$, $La_2O_3$, $Ce_2O_3$ and $Hf_2O_3$ respectively, is prepared.

Composition 7:

In a further preferred embodiment, catalyst precursors wherein the catalytically active composition comprises catalytically active components of Sn, Cu, Ni, Co and Al are prepared.

Such catalyst precursors preferably comprise the following components:

0.2% to 5% by weight of catalytically active components of tin, calculated as SnO, 1% to 20% by weight of catalytically active components of copper, calculated as CuO, 5% to 35% by weight of catalytically active components of nickel, calculated as NiO, and 5% to 35% by weight of catalytically active components of cobalt, calculated as CoO, 15% to 80% by weight of catalytically active components of aluminium and/or zirconia, calculated as $Al_2O_3$ or $ZrO_2$ as support material, In a very particularly preferred variant of this embodiment, catalyst precursors having the aforementioned composition are obtained by precipitative application on a support material. Preferably, soluble compounds of Co and Sn are precipitated onto a finely dispersed support material as disclosed in WO 2013/072289. The soluble compounds of Sn, Co, Cu and/or Ni are preferably used in the form of their nitrates or nitrosylnitrates.

It is further preferred, that the precipitative application is carried out in the presence of a complexing agent.

The complexing agent is preferably selected from the group consisting of glycolic acid, lactic acid, hydracrylic acid, hydroxybutyric acid, hydroxyvaleric acid, malonic acid, mandelic acid, citric acid, sugar acids, tartronic acid, tartaric acid, oxalic acid, malonic acid, maleic acid, succinic acid, glutaric acid, adipic acid, glycine, hippuric acid, EDTA, alanine, valine, leucine or isoleucine.

The support material is preferably aluminum oxide or zirconium oxide or a mixture thereof. The median diameter $d_{50}$ of the particles of the support material used is preferably in the range from 1 to 500 μm, preferably 3 to 400 μm and more preferably 5 to 300 μm.

The standard deviation of the particle diameter is generally in the range from 5% to 200%, preferably 10% to 100% and especially preferably 20% to 80% of the median diameter $d_{50}$.

After the precipitative application, the catalyst precursor is generally worked up as described below, by separating catalyst precursors from the solution from which the precipitative application was effected, and washing, drying, calcining and optionally converting to the desired shape in a shaping step.

Preferably, the calcining is followed by a shaping step in which the catalyst precursor is processed to give shaped bodies, especially tablets.

The height of the tablets is preferably in the range from 1 to 10 and more preferably in the range from 1.5 to 3 mm. The ratio of height h of the tablet to the diameter D of the tablet is preferably 1:1 to 1:5, more preferably 1:1 to 2.5 and most preferably 1:1 to 1:2.

If the catalyst precursor is used in the form of powder or spall, the median diameter of the particles $d_{50}$ is generally in the range from 50 to 2000 μm, preferably 100 to 1000 μm and more preferably 300 to 700 μm. The standard deviation of the particle diameter is generally in the range from 5% to 200%, preferably 10% to 100% and especially preferably 20% to 80% of the median diameter $d_{50}$.

In a particularly preferred embodiment, the median diameter $d_{50}$ of the particles of the powder or spall used is preferably in the range from 1 to 500 μm, preferably 3 to 400 μm and more preferably 5 to 300 μm. The standard deviation of the particle diameter is generally in the range from 5% to 200%, preferably 10% to 100% and especially preferably 20% to 80% of the median diameter $d_{50}$.

Preparation of the Catalyst Precursors:

The catalyst precursors can be prepared in step a) by known processes, for example by precipitation reactions (e.g. coprecipitation or precipitative application) or impregnation.

Precipitation Reactions—Coprecipitation:

Catalyst precursors can be prepared via a coprecipitation of soluble compounds of the active metals or added catalyst elements with a precipitant. For this purpose, one or more soluble compounds of the corresponding active metals and optionally one or more soluble compounds of the added catalyst elements in a liquid is admixed with a precipitant while heating and stirring until the precipitation is complete.

The liquid used is generally water.

Useful soluble compounds of the active metals typically include the corresponding metal salts, such as the nitrates or nitrosylnitrates, chlorides, sulfates, carboxylates, especially the acetates, or nitrates or nitrosylnitrates, of the aforementioned metals.

The soluble compounds of the added catalyst elements that are used are generally water-soluble compounds of the added catalyst elements, for example the water-soluble nitrates or nitrosylnitrates, chlorides, sulfates, carboxylates, especially the acetate or nitrates or nitrosylnitrates.

Precipitation Reactions—Precipitative Application:

Catalyst precursors can also be prepared by precipitative application.

Precipitative application is understood to mean a preparation method in which one or more support materials are suspended in a liquid and then soluble compounds of the active metals, such as soluble metal salts of the active metals, and optionally soluble compounds of the added catalyst elements are added, and these are then applied by precipitative application to the suspended support material by addition of a precipitant (described, for example, in EP-A2-1 106 600, page 4, and A. B. Stiles, Catalyst Manufacture, Marcel Dekker, Inc., 1983, page 15).

The soluble compounds of the active metals or added catalyst elements that are used are generally water-soluble compounds of the active metals or added catalyst elements, for example the water-soluble nitrates or nitrosylnitrates, chlorides, sulfates, carboxylates, especially the acetate or nitrates or nitrosylnitrates.

The support material is generally in the form of powder or spall.

The size of the particles is generally in the range from 50 to 2000 μm, preferably 100 to 1000 μm and more preferably 300 to 700 μm.

The support materials that are used in the precipitative application may be used, for example, in the form of spall, powders or shaped bodies, such as strands, tablets, spheres or rings. Preference is given to using support materials that already have the preferred shape and geometry described hereinafter (see section "Shape and geometry of the support materials and catalyst precursors").

The liquid used, in which the support material is suspended, is typically water.

Precipitation Reactions—General:

Typically, in the precipitation reactions, the soluble compounds of the active metals or added catalyst elements are precipitated as sparingly soluble or insoluble, basic salts by addition of a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be conducted, for example, at temperatures of 20 to 100° C., particularly 30 to 90° C., especially at 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals or semimetals used. With regard to the filterability of the precipitates, it may prove to be favorable for them to be aged— meaning that they are left to themselves for a certain time after precipitation, optionally under hot conditions or with air being passed through.

Impregnation:

The catalyst precursors can also be prepared by impregnating support materials with soluble compounds of the active metals or added catalyst elements (impregnation).

The support materials that are used in the impregnation may be used, for example, in the form of spall, powders or shaped bodies, such as strands, tablets, spheres or rings. Preference is given to using support materials that already have the preferred shape and geometry of the shaped bodies described hereinafter (see section "Shape and geometry of the support materials and catalyst precursors").

The abovementioned support materials can be impregnated by the customary processes (A. B. Stiles, Catalyst Manufacture—Laboratory and Commercial Preparations, Marcel Dekker, New York, 1983), for example by applying a salt of the active metals or added catalyst elements in one or more impregnation stages.

Useful salts of the active metals or of the added catalyst elements generally include water-soluble salts such as the carbonates, nitrates or nitrosylnitrates, carboxylates, especially the nitrates or nitrosylnitrates, acetates or chlorides, of the corresponding active metals or added catalyst elements, which are generally converted at least partly to the corresponding oxides or mixed oxides under the conditions of the calcination.

The impregnation can also be effected by the "incipient wetness method", in which the support material is moistened with the impregnation solution up to a maximum of saturation, according to its water absorption capacity, or the support material is sprayed with the impregnation solution. Alternatively, impregnation may take place in supernatant solution.

In the case of multistage impregnation processes, it is appropriate to dry and optionally to calcine between individual impregnation steps. Multistage impregnation should be employed advantageously when the support material is to be contacted with salts in a relatively large amount.

For application of multiple active metals and/or added catalyst elements and/or basic elements to the support material, the impregnation can be effected simultaneously with all salts or in any sequence of the individual salts in succession.

Preferred combinations of composition and catalyst precursor preparation methods:

In a preferred embodiment, the catalyst precursors with the previously described composition are prepared by coprecipitation or precipitative application, more preferably by precipitative application.

In an especially preferred embodiment, the catalyst precursors having one of the preferred compositions 1 to 7 are prepared by coprecipitation or precipitative application. Most preferably, catalyst precursors of one of the compositions 1 to 7 are prepared by precipitative application.

Workup of the Catalyst Precursors:

The catalyst precursors prepared during step a) by the previously described impregnation methods or precipitation methods are typically further processed by performing one or more of the following processing steps before submitting the catalyst precursor to step b):

aa) liquid separation, and
ab) washing,
ac) drying,
ad) calcination, and
ae) shaping.

Preferably, the further processing of the catalyst precursors comprises all of the above-mentioned processing steps, but it is possible to omit one or more of the above-mentioned steps and to optionally conduct the omitted processing step after the post-impregnation step b).

Separation and Washing:

The impregnated catalyst precursors or the precipitates obtained by the precipitation methods are generally separated from the liquid in which the catalyst precursors were prepared and washed.

Processes for separating and washing the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.o05_o02).

The wash liquid used is generally a liquid in which the separated catalyst precursor is sparingly soluble but which is a good solvent for impurities adhering to the catalyst, for example precipitant. A preferred wash liquid is water.

In batch preparation, the separation is generally effected with frame filter presses. The washing of the filter residue with wash liquid can be effected here by passing the wash liquid in countercurrent direction to the filtration direction.

In continuous preparation, the separation is generally effected with rotary drum vacuum filters. The washing of the filter residue is typically effected by spraying the filter residue with the wash liquid.

The catalyst precursor can also be separated off by centrifugation. In general, the washing here is effected by adding wash liquid in the course of centrifuging.

Drying:

The catalyst precursor separated off is generally dried.

Processes for drying the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.o05_o02).

The drying is effected here at temperatures in the range from preferably 60 to 200° C., especially from 80 to 160° C. and more preferably from 100 to 140° C., where the drying time is preferably 6 h or more, for example in the range from 6 to 24 h. However, depending on the moisture content of the material to be dried, shorter drying times, for example about 1, 2, 3, 4 or 5 h, are also possible.

The washed catalyst precursor that has been separated off can be dried, for example, in chamber ovens, drum driers, rotary kilns or belt driers.

The catalyst precursor can also be dried by spray-drying a suspension of the catalyst precursor.

Calcination:

In general, the catalyst precursors are calcined after the drying.

During the calcination, thermally labile compounds of the active metals or added catalyst elements, such as carbonates, hydrogencarbonates, nitrates or nitrosylnitrates, chlorides, carboxylates, oxide hydrates or hydroxides, are at least partly converted to the corresponding oxides and/or mixed oxides.

The calcination is generally effected at a temperature in the range from 250 to 1200° C., preferably 300 to 1100° C. and especially from 500 to 1000° C.

The calcination can be effected under any suitable gas atmosphere, preference being given to air and/or air mixtures, such as lean air. The calcination can alternatively be effected in the presence of hydrogen, nitrogen, helium, argon and/or steam or mixtures thereof.

The calcination is generally effected in a muffle furnace, a rotary kiln and/or a tunnel kiln, the calcination time preferably being 1 h or more, more preferably in the range from 1 to 24 h and most preferably in the range from 2 to 12 h.

Shape and Geometry of the Support Materials or Catalyst Precursors:

The catalyst precursors or the support material are preferably used in the form of powder or spall or in the form of shaped bodies.

If the catalyst precursor is used in the form of powder or spall, the median diameter of the particles $d_{50}$ is generally in the range from 50 to 2000 μm, preferably 100 to 1000 μm and more preferably 300 to 700 μm. The standard deviation of the particle diameter is generally in the range from 5% to 200%, preferably 10% to 100% and especially preferably 20% to 80% of the median diameter $d_{50}$.

In a particularly preferred embodiment, the median diameter $d_{50}$ of the particles of the powder or spall used is preferably in the range from 1 to 500 μm, preferably 3 to 400 μm and more preferably 5 to 300 μm. The standard deviation of the particle diameter is generally in the range from 5% to 200%, preferably 10% to 100% and especially preferably 20% to 80% of the median diameter $d_{50}$.

If the catalyst precursor is used in the form of shaped bodies, these are preferably used in the form of tablets.

The height of the tablets is preferably in the range from 1 to 10 and more preferably in the range from 1.5 to 3 mm. The ratio of height h of the tablet to the diameter D of the tablet is preferably 1:1 to 1:5, more preferably 1:1 to 2.5 and most preferably 1:1 to 1:2.

However, the support materials or catalyst precursors can also preferably be used in the form of shaped bodies in the process of the invention.

Suitable shaped bodies are shaped bodies having any geometry or shape. Preferred shapes are tablets, rings, cylinders, star extrudates, wagonwheels or spheres, particular preference being given to tablets, rings, cylinders, spheres or star extrudates. Very particular preference is given to the cylinder shape.

In the case of spheres, the diameter of the sphere shape is preferably 20 mm or less, more preferably 10 mm or less, even more preferably 5 mm or less and especially preferably 3 mm or less.

In a preferred embodiment, in the case of spheres, the diameter of the sphere shape is preferably in the range from 0.1 to 20, more preferably 0.5 to 10 mm, even more preferably 1 to 5 mm and especially preferably 1.5 to 3 mm.

In the case of strands or cylinders, the ratio of length: diameter is preferably in the range from 1:1 to 20:1, more preferably 1:1 to 14:1, even more preferably in the range from 1:1 to 10:1 and especially preferably in the range from 1:2 to 6:1.

The diameter of the strands or cylinders is preferably 20 mm or less, more preferably 15 mm or less, even more preferably 10 mm or less and especially preferably 3 mm or less.

In a preferred embodiment, the diameter of the strands or cylinders is preferably in the range from 0.5 to 20 mm, more preferably in the range from 1 to 15 mm, most preferably in the range from 1.5 to 10 mm.

In the case of tablets, the height h of the tablet is preferably 20 mm or less, more preferably 10 mm or less, even more preferably 5 mm or less and especially preferably 3 mm or less.

In a preferred embodiment, the height h of the tablet is preferably in the range from 0.1 to 20 mm, more preferably in the range from 0.5 to 15 mm, even more preferably in the range from 1 to 10 mm and especially preferably in the range from 1.5 to 3 mm.

The ratio of height h (or thickness) of the tablet to the diameter D of the tablet is preferably 1:1 to 1:5, more preferably 1:1 to 1:2.5 and most preferably 1:1 to 1:2.

The shaped body used preferably has a bulk density (to EN ISO 6) in the range from 0.1 to 3 kg/l, preferably from 1.0 to 2.5 kg/l and especially preferably 1.2 to 1.8 kg/l.

Shaping:

In the production of the catalyst precursors by impregnation or by precipitative application, preference is given to using support materials that already have the above-described preferred shape and geometry.

Support materials or catalyst precursors that do not have the above-described preferred shape can be subjected to a shaping step.

In the course of shaping, the support materials or catalyst precursors are generally conditioned by adjusting them to a particular particle size by grinding.

After the grinding, the conditioned support material or the conditioned catalyst precursor can be mixed with further additives, such as shaping aids, for example graphite, binders, pore formers and pasting agents, and processed further to give shaped bodies. Preferably, the catalyst precursor is mixed only with graphite as shaping aid, and no further additives are added in the course of shaping.

Standard processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff.].

Standard processes for shaping are, for example, extrusion, tableting, i.e. mechanical pressing, or pelletizing, i.e. compaction by circular and/or rotating movements.

The shaping operation can give shaped bodies with the abovementioned geometry.

The shaping can alternatively be effected by spray-drying a suspension of the catalyst precursor.

The conditioning or shaping is generally followed by a heat treatment. The temperatures in the heat treatment typically correspond to the temperatures in the calcination.

Step b) Contacting of the Catalyst Precursor Prepared in Step a) with a Re Compound:

According to the invention, the catalyst precursor prepared in step a) is contacted with a soluble Re compound.

In a preferred embodiment, the catalyst precursor is contacted with at least one additional active metal and/or at least one additional added catalyst element.

Preferably, the catalyst precursor prepared in step a) is simultaneously contacted with a soluble Re compound and at least one soluble compound of an active metal and/or an added catalyst element other than Re.

In another preferred embodiments, the catalyst precursor prepared in step a) is contacted with at least one soluble compound of an active metal and/or an added catalyst element other than Re before or after being brought in contact with the soluble Re compound.

Preferred additional active metals or additional added catalyst elements which are brought into contact with the catalyst precursor prepared in step a) are Ru, Co, Ni and Cu. More preferred additional active metals or additional added catalyst elements are Co and Ru.

The contacting of the catalyst precursor with the soluble Re compound and optionally with at least one soluble compound of an active metal and/or an added catalyst element is usually effected by contacting the catalyst precursor with one or more impregnation solutions. Impregnation solutions are solutions, which comprise a soluble Re compound and/or a soluble compound of an active metal and/or an added catalyst element and a solvent for the respective soluble compounds.

The solvent used for the preparation of the impregnation solution is preferably water, but other solvents, such as organic solvents, like alcohols and ethers, may also be used.

If the impregnation solution comprises a soluble Re compound, then the Re content of the impregnation solution is typically in the range of 0.1 to 50% by weight, preferably 1 to 40 by weight and more preferably 2 to 15% by weight.

If the impregnation solutions comprises a soluble compound of an active metal or an added catalyst element other than Re, then the content of each active metal or added catalyst element is typically in the range of 0.1 to 50% by weight, preferably 1 to 40 by weight and more preferably 2 to 15% by weight, wherein the sum of all active elements or added catalyst elements in the impregnation solutions is typically in the range of 0.1 to 70% by weight, preferably in the range of 1 to 60% by weight and more preferably in the range of 2 to 50% by weight.

If the impregnation solution comprises a soluble Ru compound, then the Ru content of the impregnation solution is typically in the range of 0.1 to 50% by weight, preferably 1 to 40 by weight and more preferably 2 to 15% by weight.

If the impregnation solution comprises a soluble Co compound, then the Co content of the impregnation solution is typically in the range of 0.1 to 20% by weight, preferably 0.1 to 5 by weight and more preferably 0.15 to 2% by weight.

Preferably, the impregnation solutions comprise three components, namely a soluble Re compound, a soluble Ru compound and a soluble Co compound.

As a soluble Re compound, preferably perrhenic acid is used.

Soluble compounds of the active metals or added catalyst elements are generally employed in the form of their water-soluble salts, such as their carbonates, halides, nitrates, nitrosylnitrates or carboxylates. Preferably, water soluble salts of the active metals or added catalyst elements in the form of the respective nitrates or nitrosylnitrates, acetates or chlorides are employed as soluble compounds. Most preferably, the nitrate or nitrosylnitrate salts are employed as soluble compounds of the active metals or added catalyst elements.

If the catalyst precursor is to be contacted with a Co and/or Ru compound, then preferably cobalt nitrate hexahydrate is used as a soluble compound of Co and Ru-nitrosyl nitrate is used as soluble compound of Ru.

The contacting of the catalyst precursors prepared in step a) with the impregnation solution(s) in step b) is preferably effected after the calcination of the catalyst precursor prepared in step a) or after the heat treatment after the shaping step and prior to the reduction/passivation of the catalyst precursor.

The contacting of the catalyst precursor prepared in step a) with an impregnation solution is referred hereinafter as post-impregnation.

The catalyst precursors that are used in post-impregnation may be used, for example, in the form of spall, powders or shaped bodies, such as strands, cylinders, tablets, spheres or rings. Preference is given to using catalyst precursors that have the above-described shape and geometry (see section "Shape and geometry of the support materials and shaped bodies"). Particular preference is given to using catalyst precursors in the form of tablets.

The height of the tablets is preferably in the range from 1 to 10 and more preferably in the range from 1.5 to 3 mm. The ratio of height h of the tablet to the diameter D of the tablet is preferably 1:1 to 1:5, more preferably 1:1 to 2.5 and most preferably 1:1 to 1:2.

In a particularly preferred embodiment, the median diameter $d_{50}$ of the particles of the powder or spall used is preferably in the range from 1 to 500 μm, preferably 3 to 400 μm and more preferably 5 to 300 μm. The standard deviation of the particle diameter is generally in the range from 5% to 200%, preferably 10% to 100% and especially preferably 20% to 80% of the median diameter $d_{50}$.

The catalyst precursors can be post-impregnated by the customary processes (A. B. Stiles, Catalyst Manufacture—Laboratory and Commercial Preparations, Marcel Dekker, New York, 1983).

The post-impregnation of the catalyst precursors can be effected by the "incipient wetness method", in which the catalyst precursor is moistened with the impregnation solution up to a maximum of saturation, according to its solvent, in particular water, absorption capacity. Alternatively, post-impregnation can be effected in supernatant solution.

In a preferred embodiment, post-impregnation of the catalyst precursors is effected by the "incipient wetness method" by first determining the saturation capacity (SC) of the catalyst precursor with the solvent used in the impregnation solutions, which is most preferably water, and then contacting the catalyst precursor with an amount of impregnation solution, which corresponds to 50 to 100%, preferably 60 to 95% and more preferably 70 to 90% of the previously determined saturation capacity (SC).

Post-impregnation can be conducted in one or more steps.

If the post-impregnation is to be carried out in one step, then the impregnation solution should comprise all compounds which are to be contacted with the catalyst precursor, e.g. the soluble compounds of Re and optionally at least one additional soluble compound of the active metals or added catalyst elements. As previously described, the impregnation solutions used for one-step impregnation preferably comprise soluble compounds of Co and/Ru in addition to soluble Re compounds.

If the post-impregnation is to be carried out in two or more steps, then the post-impregnation can be repeated one or more times using an impregnation solution having the same composition as the one which with the catalyst precursor was previously contacted. Alternatively, the catalyst precursor can be subsequently post-impregnated with impregnation solutions of different compositions.

Preferably, post-impregnation is carried out in two or more steps, wherein an impregnation solution of the same composition is used.

In a most preferred embodiment, post-impregnation is carried out by applying the incipient wetness method, wherein in a first step the catalyst precursor is brought into contact with an amount of impregnation solution, which corresponds to 50 to 100%, preferably 60 zo 95% and more preferably 70 to 90% of the solvent capacity (SC) of the catalyst precursor and wherein a second step the catalyst precursor obtained in the first step is brought into contact with an amount of impregnation solution having the same composition as the impregnation solution used in the first step, which corresponds to 50 to 100%, preferably 60 to 95% and most preferably 70 to 90 of the originally determined solvent capacity (SC) of the catalyst precursor.

If post-impregnation is carried out in two or more steps, the catalyst precursor is preferably dried after each post-impregnation step. The conditions of the drying step conducted after each post-impregnation step are usually the same as the conditions previously described under the section "Drying" above.

Optionally, the respective drying step after each post-impregnation step may also be followed by a calcination. It is preferable, however, that the respective drying step is not followed by a subsequent calcination.

Preferably, the catalyst precursor is reduced after the last drying step, as described hereinafter.

The contacting of the catalyst precursor with the soluble compounds of Re increases the proportion of Re in the catalyst precursor by about 0.1% to 10% by weight, preferably 0.5% to 7% by weight and most preferably by 1% to 5% by weight, based in each case on the total mass of the catalyst precursor.

In the preferred embodiments in which the catalyst precursor is contacted with a soluble compound of an active metal or added catalyst element other than Re, the portion of the added active metal or added catalyst element is generally increased by 0.1 to 10% by weight, preferably 0.5 to 7% by weight and more preferably 1 to 5% by weight, based in each case on the total mass of the catalyst precursor.

In the most preferred embodiments in which the catalyst precursor is contacted with a soluble compound of Co, the portion of Co is generally increased by 0.1 to 5% by weight, preferably 0.3 to 4% by weight and more preferably 0.5 to 3% by weight, based in each case on the total mass of the catalyst precursor.

In the most preferred embodiments in which the catalyst precursor is contacted with a soluble compound of Ru, the portion of Ru is generally increased by 0.1 to 5% by weight, preferably 0.3 to 4% by weight and more preferably 0.5 to 3% by weight, based in each case on the total mass of the catalyst precursor.

After the catalyst precursor has been contacted with the soluble compounds of Re, the catalyst precursor, after the last drying, preferably comprises (where the weight figures are based on the total mass of the catalyst precursor) 0.1% to 20% by weight, more preferably 0.5% to 15% by weight and especially preferably 1% to 10% by weight of catalytically active components of Re, calculated as $ReO_3$.

If the catalyst precursor is contacted with a soluble compound of an active metal or an added catalyst element other than Re, the catalyst precursor, after the last drying step, preferably comprises (where the weight figures are based on the total mass of the catalyst precursor) 0.1 to 20% by weight, more preferably 0.5 to 15% by weight and most preferably 1 to 10% by weight of catalytically active components of the respective active metal or added catalyst element, calculated as the respective oxide.

If the catalyst precursor is contacted with a soluble compound of an Ru, the catalyst precursor, after the last drying step, preferably comprises (where the weight figures are based on the total mass of the catalyst precursor) 0.1 to 20% by weight, more preferably 0.5 to 15% by weight and most preferably 1 to 10% by weight of catalytically active components of Ru, calculated as $RuO_2$.

If the catalyst precursor is contacted with a soluble compound of an Co, the catalyst precursor, after the last drying step, preferably comprises (where the weight figures are based on the total mass of the catalyst precursor) 0.1% to 50% by weight, more preferably 10% to 45% by weight and especially preferably 20% to 40% by weight of catalytically active components of Co, calculated as CoO.

Preferably, the last impregnation step of step b) is followed by a drying step (as described above) and a reduction and/or passivation step According to the invention, the conversion of MEG and/or MEA and ammonia is effected over a reduced catalyst precursor.

The reduction generally converts the catalyst precursor to the catalytically active form thereof.

Accordingly, it is preferred that after the drying the catalyst precursor obtained in step b), one or more of the following processing steps are performed:

ba) Reduction, and
bb) Passivation,

Reduction:

The reduction of the catalyst precursor is preferably conducted at elevated temperature.

The reducing agent used is typically hydrogen or a hydrogen-comprising gas.

The hydrogen is generally used in technical grade purity. The hydrogen can also be used in the form of a hydrogen-comprising gas, i.e. in mixtures with other inert gases, such as nitrogen, helium, neon, argon or carbon dioxide. In a preferred embodiment, hydrogen is used together with nitrogen, where the proportion by volume of hydrogen is preferably in the range from 1% to 50%, more preferably 2.5% to 30% and especially preferably 5% to 25% by volume. The hydrogen stream can also be recycled into the reduction as cycle gas, optionally mixed with fresh hydrogen and optionally after removal of water by condensation.

It is further preferable to increase the proportion of hydrogen in the mixture with inert gas in a gradual or stepwise manner, for example from 0% by volume of hydrogen to 50% by volume of hydrogen. For instance, in the course of heating, the proportion by volume of hydrogen may be 0% by volume and, on attainment of the reduction temperature, can be increased in one or more stages or gradually to 50% by volume.

The reduction is preferably conducted in a muffle furnace, a rotary kiln, a tunnel kiln or a moving or stationary reduction oven.

The catalyst precursor is also preferably reduced in a reactor in which the catalyst precursors are arranged as a fixed bed. Particular preference is given to reducing the catalyst precursor in the same reactor in which the subsequent reaction of MEG and/or MEA with NH3 is effected.

In addition, the catalyst precursor can be reduced in a fluidized bed reactor in the fluidized bed.

The catalyst precursor is generally reduced at reduction temperatures of 50 to 600° C., especially from 100 to 500° C., more preferably from 150 to 450° C. and especially preferably 200 to 300° C.

The partial hydrogen pressure is generally from 1 to 300 bar, especially from 1 to 200 bar, more preferably from 1 to 100 bar, the pressure figures here and hereinafter relating to the pressure measured in absolute terms.

The duration of the reduction is generally dependent on the size and shape of the reactor and is generally conducted only at such a speed that a significant temperature rise in the reactor is avoided. This means that, according to the shape and size of the reactor, the reduction take several hours to several weeks.

During the reduction, a solvent can be supplied in order to remove water of reaction formed and/or in order, for example, to be able to heat the reactor more quickly and/or to be able to better remove the heat during the reduction. The solvent here may also be supplied in supercritical form.

Suitable solvents may be used the solvents described above. Preferred solvents are water; ethers such as methyl tert-butyl ether, ethyl tert-butyl ether, dioxane or tetrahydrofuran.

Particular preference is given to water or tetrahydrofuran. Suitable solvents likewise include suitable mixtures.

After the reduction, the reduced catalyst may be contacted directly with the reactants, such as MEG, MEA and NH3. This is especially advantageous when the reduction is effected in the reactor in which the subsequent conversion of MEG and/or MEA is also effected.

The catalyst thus reduced can alternatively, after the reduction, be handled under inert conditions. The catalyst precursor can preferably be handled and stored under an inert gas such as nitrogen, or under an inert liquid, for example an alcohol, water or the product of the particular reaction for which the catalyst is used. In that case, it may be necessary to free the catalyst of the inert liquid prior to commencement of the actual reaction. Storage of the catalyst under inert substances enables uncomplicated and nonhazardous handling and storage of the catalyst.

Passivation:

After the reduction, the catalyst can be contacted with an oxygen-comprising gas stream such as air or a mixture of air with nitrogen.

This gives a passivated catalyst. The passivated catalyst generally has a protective oxide layer. This protective oxide layer simplifies the handling and storage of the catalyst, such that, for example, the installation of the passivated catalyst into the reactor is simplified. For passivation, after the reduction step, the reduced catalyst is contacted with an oxygenous gas, preferably air.

The oxygenous gas may be used with additions of inert gases, such as nitrogen, helium, neon, argon or carbon dioxide. In a preferred embodiment, air is used together with nitrogen, where the proportion by volume of air is preferably in the range from 1% to 80%, more preferably 20% to 70% and especially preferably 30% to 60% by volume. In a preferred embodiment, the proportion by volume of air in the mixture with nitrogen is increased gradually from 0% to about 50% by volume.

The passivation is effected preferably at temperatures up to 50° C., preferably up to 45° C. and most preferably up to 35° C.

Activation:

Before being contacted with the reactants, a passivated catalyst is preferably reduced by treatment of the passivated catalyst with hydrogen or a hydrogen-comprising gas. The conditions in the activation generally correspond to the reduction conditions which are employed in the reduction. The activation generally removes the protective passivation layer.

Reactants:

According to the invention, the inventive conversion of ethylene glycol (EG) and/or monoethanolamine (MEA) and ammonia ($NH_3$) is effected in the presence of the reduced or activated amination catalysts in the liquid phase.

Ethylene glycol:

The ethylene glycol employed in the inventive amination of MEG is preferably industrial ethylene glycol having a purity of at least 98%, and most preferably ethylene glycol having a purity of at least 99% and most preferably of at least 99.5%.

The ethylene glycol used in the process can be prepared from ethylene obtainable from petrochemical processes. For instance, in general, ethene is oxidized in a first stage to ethylene oxide, which is subsequently reacted with water to give ethylene glycol. The ethylene oxide obtained can alternatively be reacted with carbon dioxide in what is called the omega process to give ethylene carbonate, which can then be hydrolyzed with water to give ethylene glycol. The omega process features a higher selectivity for ethylene glycol since fewer by-products, such as di- and triethylene glycol, are formed.

Ethylene used in the preparation of MEG can alternatively be prepared from renewable raw materials. For instance, ethylene can be formed by dehydration from bioethanol.

Ethylene glycol can also be prepared via the synthesis gas route, for example by oxidative carbonylation of methanol to give dimethyl oxalate and subsequent hydrogenation thereof.

Thus, a further possible petrochemical raw material for the preparation of MEG is also natural gas or coal.

MEA:

MEA may also be used in the process of the invention.

MEA can, as described above, be prepared by reacting ethylene oxide with ammonia.

Preferably, MEA can be prepared by reacting MEG with ammonia, for example by the process of the invention, by first reacting MEG with ammonia and separating the MEA formed in addition to EDA from EDA and recycling the MEA separated off, optionally together with unconverted MEG, into the preparation process of the invention.

When MEA is used in the process of the invention as without MEG, MEA is preferably used with a purity of at least 97%, and most preferably with a purity of at least 98% and most preferably of at least 99%.

When MEA is used together with MEG in the process of the invention, the proportion by weight of MEA in relation to the mass of MEA and MEG is preferably in the range from 0% to 60% by weight, more preferably 10% to 50% by weight and most preferably 20% to 40% by weight.

Ammonia:

According to the invention, ethylene glycol and/or monoethanolamine is reacted with ammonia.

The ammonia used may be conventional commercially available ammonia, for example ammonia with a content of more than 98% by weight of ammonia, preferably more than 99% by weight of ammonia, more preferably more than 99.5% by weight, in particular more than 99.8% by weight of ammonia.

Hydrogen:

The process of the invention is preferably effected in the presence of hydrogen.

The hydrogen is generally used in technical grade purity. The hydrogen can also be used in the form of a hydrogen-comprising gas, i.e. with additions of other inert gases, such as nitrogen, helium, neon, argon or carbon dioxide. Hydrogen-comprising gases used may, for example, be reformer offgases, refinery gases etc., if and as long as these gases do not comprise any catalyst poisons for the catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Reaction in the Liquid Phase:

According to the invention, ethylene glycol is reacted with ammonia and an amination catalyst in the liquid phase.

In the context of the present invention, "reaction in the liquid phase" means that the reaction conditions, such as pressure and temperature, are adjusted such that ethylene glycol is present in the liquid phase and flows around the amination catalyst in liquid form.

The reaction of MEG and/or with ammonia can be conducted continuously or batchwise.

Preference is given to a continuous reaction.

Reactors:

Suitable reactors for the reaction in the liquid phase are generally tubular reactors. The catalyst may be arranged as a moving bed or fixed bed in the tubular reactors.

Particular preference is given to reacting ethylene glycol and/or monoethanolamine with $NH_3$ in a tubular reactor in which the amination catalyst is arranged in the form of a fixed bed.

If the catalyst is arranged in the form of a fixed bed, it may be advantageous, for the selectivity of the reaction, to "dilute", so to speak, the catalysts in the reactor by mixing them with inert random packings. The proportion of the random packings in such catalyst preparations may be 20 to 80, preferably 30 to 60 and more preferably 40 to 50 parts by volume.

Alternatively, the reaction is advantageously effected in a shell and tube reactor or in a single-stream plant. In a single-stream plant, the tubular reactor in which the reaction is effected may consist of a series connection of a plurality of (e.g. two or three) individual tubular reactors. A possible and advantageous option here is the intermediate introduction of feed (comprising the reactant and/or ammonia and/or $H_2$) and/or cycle gas and/or reactor output from a downstream reactor.

Reaction Conditions:

When working in the liquid phase, the MEG and/or plus ammonia are guided simultaneously in liquid phase, including hydrogen, over the catalyst, which is typically in a preferably externally heated fixed bed reactor, at pressures of generally 5 to 30 MPa (50-300 mbar), preferably 5 to 25 MPa, more preferably 20 15 to 25 MPa, and temperatures of generally 80 to 350° C., particularly 100 to 300° C., preferably 120 to 270° C., more preferably 130 to 250° C., especially 160 to 230° C.

The partial hydrogen pressure is preferably 0.25 to 20 MPa (2.5 to 200 bar), more preferably 0.5 to 15 MPa (5 to 150 bar), even more preferably 1 to 10 MPa (10 to 100 bar) and especially preferably 2 to 5 MPa (20 to 50 bar).

Reactor Feed:

MEG and/or MEA and ammonia are supplied to the reactor preferably in liquid form and contacted in liquid form with the amination catalyst.

Either trickle mode or liquid-phase mode is possible.

It is advantageous to heat the reactants, preferably to the reaction temperature, even before they are supplied to the reaction vessel.

Ammonia is preferably used in 0.90 to 100 times the molar amount, especially in 1.0 to 20 times the molar amount, based in each case on the MEG or MEA used.

The catalyst hourly space velocity is generally in the range from 0.05 to 0.5, preferably 0.1 to 2, more preferably 0.2 to 1 kg (MEG+MEA) per kg of catalyst and hour.

At the catalyst hourly space velocities stated, the conversion of MEG or MEA is generally in the range from 20% to 75%, preferably in the range from 30% to 60% and most preferably in the range from 35% to 65%.

The water of reaction formed in the course of the reaction, one mole per mole of alcohol group converted in each case, generally has no detrimental effect on the degree of conversion, the reaction rate, the selectivity, or the catalyst lifetime, and is therefore usefully removed from the reaction product—by distillation, for example—only when said product is worked up.

Reactor Effluent:

The output or reactor effluent from the amination reactor comprises the products of the amination reaction, unconverted reactants, such as ethylene glycol and ammonia, and also hydrogen and water.

As products of the amination reaction, the output from the amination reactor also comprises the corresponding ethanolamines and/or ethyleneamines based on MEG.

The output from the amination reactor preferably comprises MEA and/or EDA.

As products from the amination reaction, the reaction output also preferably comprises higher linear ethyleneamines of the general formula

R—CH$_2$—CH$_2$—NH$_2$ where R is a radical of the formula —(NH—CH$_2$—CH$_2$)$_X$—NH$_2$ where x is an integer in the range from 1 to 4, preferably 1 to 3 and most preferably 1 to 2. Preferably, the reaction output comprises DETA, TETA and TEPA, more preferably DETA and TETA and especially preferably DETA.

As products of the amination reaction, the output from the amination reactor may also comprise higher linear ethanolamines of the formula

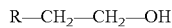
R—CH$_2$—CH$_2$—OH where R is a radical of the formula —(NH—CH$_2$—CH$_2$)$_X$—NH$_2$ where x is an integer in the range from 1 to 4, preferably 1 to 3 and most preferably 1 to 2.

One example of a higher linear ethanolamine is AEEA.

As products of the amination reaction, the reaction output may also comprise cyclic ethanolamines of the formula

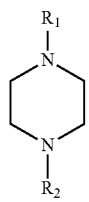

where R$_1$ is a radical of the formula —(CH$_2$—CH$_2$—NH)$_X$—CH$_2$—CH$_2$—OH where x is an integer in the range from 0 to 4, preferably 0 to 3 and more preferably 1 to 2, and R$_2$ is independently or simultaneously either H or a radical of the formula —(CH$_2$—CH$_2$—NH)$_X$—CH$_2$—CH$_2$—OH where x is an integer in the range from 0 to 4, preferably 0 to 3 and more preferably 1 to 2, or a radical of the formula —(CH$_2$—CH$_2$—NH)$_X$—CH$_2$—CH$_2$—NH$_2$ where x is an integer in the range from 0 to 4, preferably 0 to 3 and more preferably 1 to 2. One example of a cyclic ethanolamine is hydroxyethylpiperazine (HEP).

As products of the amination reaction, the reaction output may also comprise cyclic ethyleneamines of the general formula

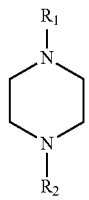

where R$_1$ and R$_2$ are independently or simultaneously either H or a radical of the formula —(CH$_2$—CH$_2$—NH)$_X$—CH$_2$—CH$_2$—NH$_2$ where X is an integer in the range from 0 to 4, preferably 0 to 4 and more preferably 1 to 2.

Examples of cyclic ethyleneamines present in the reaction output are piperazine and AEPIP.

The output preferably comprises 1% to 60% by weight of MEA, 1% to 90% by weight of EDA, 0.1% to 30% by weight of higher cyclic ethyleneamines, such as PIP and AEPIP, 0.1% to 30% by weight of higher linear ethyleneamines, such as DETA, TETA and TEPA.

The output more preferably comprises 10% to 50% by weight of MEA, 25% to 85% by weight of EDA, 0.25% to 10% by weight of cyclic ethyleneamines, such as PIP and AEPIP, 1% to 30% by weight of higher linear ethyleneamines, such as DETA, TETA and TEPA.

The output most preferably comprises 15% to 45% by weight of MEA, 30% to 70% by weight of EDA, 0.5% to 5% by weight of cyclic ethyleneamines, such as PIP and AEPIP, 5% to 25% by weight of higher linear ethyleneamines, such as DETA, TETA and TEPA.

The process of the invention can achieve selectivity quotients SQ of 1.5 or more, preferably 4 or more and more preferably of 8 or more. This means that the product ratio of desired linear ethyleneamines and ethanolamines, such as MEA and EDA, to unwanted cyclic ethyleneamines and unwanted higher ethanolamines, such as PIP and AEEA, can be increased by the process of the invention.

The output is generally worked up, such that the different components are separated from one another.

For this purpose, the reaction output is appropriately decompressed.

The components that are in gaseous form after the decompression, such as hydrogen and inert gases, are generally separated from the liquid components in a gas-liquid separator. The gaseous components can be recycled into the amination reactor individually (after a further workup step) or together.

After hydrogen and/or inert gas has been separated off, the output from the amination reactor optionally comprises ammonia, unconverted ethylene glycol, water and the amination products.

Preferably, the output from the amination reactor is separated in two separation sequences, where each separation sequence comprises a multistage distillation. Such a workup is described, for example, in EP-B1-198699. Accordingly, in the first separation sequence, water and ammonia are first separated off and, in the second separation sequence, a separation into unconverted MEG, and MEA, EDA, PIP, DETA, AEEA and higher ethyleneamines. In this case, lower- and higher-boiling components relative to the azeotrope of MEG and DETA are first removed and then the mixture that has been concentrated in MEG and DETA is separated by extractive distillation with triethylene glycol (TEG) as selective solvent into a stream comprising MEG and DETA.

MEA can be recycled partly or fully into the process of the invention with unconverted MEG, optionally together or separately.

Advantages:

In the process of the invention, it is possible to convert MEG with a high selectivity for the linear amination products MEA and EDA, while the selectivity for the cyclic amination product PIP and the higher ethanolamine AEEA is low.

A measure of this effect is the selectivity quotient SQ which is defined as the quotient of the sum total of the selectivities of DETA and EDA and the sum total of the selectivities of PIP and AEEA (SQ=(S(DETA)+S(EDA))/(S(PIP)+S(AEEA)).

The achievement of a high selectivity quotient SQ is industrially advantageous since the market demand for the linear amination products MEA and EDA and their higher homologs, such as DETA and TETA, is higher than the demand for PIP or AEEA.

In addition, the process of the invention forms a lower level of unwanted by-products. Unwanted by-products are, for example, gaseous breakdown products or insoluble or sparingly soluble oligomers and polymers based on MEA and EDA. The formation of such by-products leads to a reduction in the carbon balance and hence to a reduction in the economic viability of the process. The formation of sparingly soluble or insoluble by-products can lead to deposition on the amination catalysts which reduces the activity of the amination catalysts.

The process of the invention likewise leads to a reduction in the amount of N-methylethylenediamine (NMEDA). NMEDA is an unwanted by-product. In many industrial applications, a purity of EDA is specified where the proportion of NMEDA is below 500 ppm by weight.

In addition, it has been found that the catalyst precursors used in the process of the invention have a high activity in the process, and so a favorable space-time yield can be achieved.

Overall, the process of the invention can achieve an advantageous spectrum of properties in relation to overall selectivity, selectivity quotient, activity and the formation of unwanted by-products.

The invention is illustrated by the following examples:

EXAMPLE 1: PREPARATION OF THE CATALYST PRECURSOR (STEP A))

A catalyst precursor was obtained according to example B3 of WO 2013/072289. The tablets (3×3 mm) obtained in this way were comminuted to spall of 1 to 2 mm in size. The solvent capacity SC of the spall for water was determined to be 0.29 ml/g.

Examples 2 to 13: Preparation of the Catalysts (Step b)) by Post-Impregnation of the Catalyst Precursor Prepared in Example 1

Aqueous metal salt solutions (impregnation solutions) were prepared according to Table 1 and used for the post-impregnation of the catalyst precursor obtained in Example 1. The metal content of the aqueous metal salt solutions was as follows:

Perrhenic acid: 50 g Re per 100 g
Ru-nitrosylnitrate: 20 g Ru per 100 g
Co-nitrate hexahydrate: 20 g Co per 100 g.

The impregnation solutions were obtained by mixing the amounts of each aqueous metal salt solution as depicted in Columns 2 to 4 of Table 1 and adding additional water to obtain impregnation solutions having the total volume set out in Column 5 of Table 1.

Post-impregnation was carried out in an impregnation apparatus by the incipient wetness method, wherein the respective impregnation solutions were added in an amount corresponding to x % (see Column 9 of Table 1) of the solvent capacity SC determined in Example 1. The post-impregnated spall was revolved for 30 minutes in the impregnation apparatus to achieve a homogeneous uptake of the metal salt solutions by the spall. In case of a one-step post-impregnation, the post-impregnated spall was subsequently dried for 16 hours at 120° C. in a drying chamber. In case of a two-step post-impregnation, the post-impregnated spall obtained during the first post-impregnation step was dried in the impregnation apparatus under a water-jet vacuum at 120° C. for 4 hours before the second post-impregnation step was performed. The second post-impregnation step was also carried out by the incipient wetness method by adding an amount of metal salt solution corresponding to x % of the solvent capacity determined in Example 1 (see Column 9 of Table 1). The drying step after the second post-impregnation step was carried out for 4 hours under a water jet vacuum at 120° C.

The theoretical metal content of the catalyst precursors after the last drying step is depicted in Columns 6 to 8 of Table 1.

TABLE 1

| Example. | Perrhenic acid (g) | Ruthenium-nitrosyl-nitrat-solution. (g) | Cobalt-nitrate-hexahydrate (g) | Total Volume of Mixed Metal Salt Solution after Addition of Water | Theor Re-content. (% by weight per 100 g) | Theor Ru-content. (% by weight per 100 g) | Theor Co-content. (% by weight per 100 g) | Impregnation[1] |
|---|---|---|---|---|---|---|---|---|
| 2 | 2.6 | 18.4 | 7.0 | 39 | 0.9 | 2.0 | 0.9 | 1* 90% SC |
| 3 | 13.8 | 18.7 | 7.1 | 39 | 5.0 | 2.0 | 1.0 | 1* 90% SC |
| 4 | 6.7 | 9.2 | 7.1 | 70 | 2.4 | 1.0 | 1.0 | 2* 90%/ 70% SC |
| 5 | 6.9 | 18.7 | 7.1 | 70 | 2.5 | 2.0 | 1.0 | 2* 90%/ 70% SC |

TABLE 1-continued

| Example. | Perrrhenic acid (g) | Ruthenium-nitrosyl-nitrat-solution. (g) | Cobalt-nitrate-hexahydrate (g) | Total Volume of Mixed Metal Salt Solution after Addition of Water | Theor Re-content. (% by weight per 100 g) | Theor Ru-content. (% by weight per 100 g) | Theor Co-content. (% by weight per 100 g) | Impregnation[1] |
|---|---|---|---|---|---|---|---|---|
| 6 | 29.1 | 24.9 | 7.7 | 70 | 10.5 | 2.7 | 1.0 | 2* 90%/70% SC |
| 7 | 3.3 | 5.6 | 3.5 | 70 | 1.2 | 0.6 | 0.5 | 2* 90%/70% SC |
| 8 | 8.5 | 23.3 | 5.8 | 70 | 3.1 | 2.5 | 0.8 | 2* 90%/70% SC |
| 9 | 4.3 | 14.5 | 4.6 | 70 | 1.6 | 1.6 | 0.6 | 2* 80% SC |
| 10 | 3.1 | 10.5 | 3.0 | 70 | 1.1 | 1.1 | 0.4 | 2* 80% SC |
| 11 | 11.6 | 0.0 | 0.0 | 39 | 4.2 | 0.0 | 0.0 | 1* 90% SC |
| 12 (Comparative Example) | 0.0 | 18.2 | 7.0 | 39 | 0.0 | 2.0 | 0.9 | 1* 90% SC |
| 13 (Comparative Example) | 0 | 0 | 0 | 0 | | | | |

[1]One step post-impregnation is designated as "1*". Two-step post-impregnation is designated as "2*".

The catalyst precursor obtained in this manner was reduced by reductive calcination according to Comparative Example 4 in WO 2018/224316 and subsequently passivated as in WO 2018/224316, Comparative Example 1.

Testing of the Catalysts:

The testing of the catalysts was carried out as described in WO 2018/224316, page 37, except that the testing was conducted at a temperature of 170° C. and a catalyst hourly space velocity in the range of 0.3 to 0.6 kg/l/h (see Column 3 of Table 2).

The results of the testing are summarized in Table 2.

For a better comparison, the testing results (selectivity S of the respective products) at different hourly space velocities were evaluated in a manner that load depending measurement values in the range of 25 to 35% conversion and in a range of 35 to 45% conversion were linearly interpolated to a conversion of 35%.

TABLE 2

| Catalyst Precursor from Example Nr. | Conversion % | MEG-hourly space velocity g/ml/h | SQ | S EDA % | S MEOA % | S PIP % | S DETA % | S AEEA % |
|---|---|---|---|---|---|---|---|---|
| 12 (Comparative Example) | 35 | 0.38 | 4.4 | 49.0 | 29.3 | 9.2 | 5.9 | 3.6 |
| 2 | 35 | 0.37 | 4.8 | 51.6 | 27.1 | 9.2 | 5.9 | 3.2 |
| 3 | 35 | 0.46 | 5.6 | 51.1 | 31.7 | 7.5 | 4.4 | 2.8 |
| 4 | 35 | 0.39 | 4.7 | 49.1 | 30.3 | 8.5 | 5.6 | 3.2 |
| 5 | 35 | 0.43 | 5.0 | 52.1 | 27.5 | 8.3 | 5.6 | 3.0 |
| 6 | 35 | 0.50 | 5.6 | 50.9 | 30.7 | 7.1 | 5.7 | 3.1 |
| 7 | 35 | 0.39 | 4.6 | 48.7 | 30.5 | 8.6 | 5.4 | 3.2 |
| 8 | 35 | 0.42 | 5.1 | 49.9 | 30.6 | 8.0 | 5.6 | 3.1 |
| 9 | 35 | 0.40 | 4.9 | 50.2 | 30.1 | 8.2 | 5.5 | 3.1 |
| 10 | 35 | 0.44 | 5.0 | 50.7 | 29.5 | 8.3 | 5.1 | 3.1 |
| 13 (Comparative Example) | 35 | 0.17 | 3.8 | 45.9 | 34.9 | 7.4 | 4.4 | 5.0 |
| 11 | 35 | 0.44 | 4.7 | 47.8 | 32.7 | 8.1 | 5.2 | 3.4 |

It is evident that the post-impregnation of catalyst precursors with Co and Ru (Comparative Example 12) compared to non-impregnated catalyst precursors (Comparative Example 13) already leads to an increase of the selectivity quotient SQ (SQ=(S(DETA)+S(EDA))/(S(PIP)+S(AEEA))) from 3.8 to 4.4.

An increase of SQ corresponds to an increase of the sum of the selectivity of the desired products EDA and DETA and a decrease of the sum of the selectivity of the undesired products PIP and AEEA.

If the post-impregnation is carried out with Re (Example 11) instead of Co and Ru (Comparative Example 12), it becomes evident that the post-impregnation with Re without a post-impregnation of Co and Ru results in a further increase of SQ from 4.4 to 4.7.

If post-impregnation is carried out with Re in combination with Ru and Co (Examples 2 to 10), further increases of SQ to values of up to 5.6 are achieved.

The invention claimed is:

1. A process for preparing alkanolamines and ethyleneamines in the liquid phase, by reacting ethylene glycol, monoethanolamine, or a combination thereof with ammonia in the presence of an amination catalyst which is obtained by reducing a catalyst precursor, wherein the preparation of the catalyst precursor comprises a step a) in which a catalyst precursor comprising one or more catalytically active components of Sn, Cu and Ni is prepared by coprecipitation or by precipitative application, and a step b) in which the catalyst precursor prepared in step a) is contacted with a soluble Re compound by post-impregnating the catalyst precursor with an impregnating solution comprising the soluble Re compound.

2. The process according to claim 1, wherein the catalyst precursor prepared in step a) additionally comprises catalytically active components of Co.

3. The process according to claim 1, wherein the catalyst precursor in step a) is prepared by coprecipitation and comprises in the range from 1% to 95% by weight of catalytically active components selected from the group consisting of Sn, Cu, Ni, and mixtures thereof, calculated as CuO, NiO and SnO respectively and based in each case on the total mass of the catalyst precursor.

4. The process according to claim 1, wherein the catalyst precursor is prepared by precipitative application in step a) and, comprises in the range from 5% to 95% by weight of support material and in the range from 5% to 90% by weight of catalytically active components selected from the group consisting of Sn, Cu, Ni, and mixtures thereof, calculated as CuO, NiO and SnO respectively and based in each case on the total mass of the catalyst precursor.

5. The process according to claim 2, wherein the catalyst precursor prepared in step a) comprises,
  0.2% to 5% by weight of catalytically active components of tin, calculated as SnO,
  1% to 20% by weight of catalytically active components of copper, calculated as CuO,
  5% to 35% by weight of catalytically active components of nickel, calculated as NiO, and
  5% to 35% by weight of catalytically active components of cobalt, calculated as CoO, and
  15% to 80% by weight of catalytically active components of aluminum, calculated as $Al_2O_3$ as support material, based on the total mass of the catalyst precursor.

6. The process according to claim 5, wherein the catalyst precursor is prepared in the presence of tin nitrate and a complexing agent.

7. The process according to claim 1, wherein the Re concentration in the impregnating solution is in the range of 0.1 to 50% by weight.

8. The process according to claim 1, wherein the catalyst precursor in step b) is contacted with a soluble compound of an active metal or an added catalyst element other than Re.

9. The process according to claim 1, wherein the catalyst precursor in step b) is contacted with a soluble Ru compound and/or a soluble Co compound by post-impregnating the catalyst precursor with an impregnating solution comprising a soluble Ru compound and/or a soluble Co compound and the Ru concentration in the impregnating solution being in the range of 0.1 to 50% by weight or the Co concentration in the impregnating solution being in the range of 0.1 to 20% by weight.

10. The process according to claim 1, wherein the catalyst precursor is dried after step b) before reducing the catalyst precursor to obtain the amination catalyst.

11. The process according to claim 10, wherein the catalyst precursor comprises 0.1% to 20% by weight of catalytically active components of Re, calculated as $ReO_3$ and based on the total mass of the catalyst precursor after the last drying step.

12. The process according to claim 10, wherein the catalyst precursor comprises 0.1% to 50% by weight of catalytically active components of Co, calculated as CoO and based on the total mass of the catalyst precursor after the last drying step or wherein the catalyst precursor comprised 0.1% to 50% by weight of catalytically active components of Ru, calculated as $RuO_2$ and based on the total mass of the catalyst precursor after the last drying step.

13. The process according to claim 1, wherein the catalyst precursors prepared in step a) are further processed by performing one or more of the following processing steps before submitting the catalyst precursor to step b):
  aa) liquid separation,
  ab) washing,
  ac) drying,
  ad) calcination,
  ae) shaping.

14. The process according to claim 1, wherein the reaction of ethylene glycol or monoethanolamine with ammonia is effected in the liquid phase at a pressure of 5 to 30 MPa and a temperature in the range from 80 to 350° C.

* * * * *